US00PP25108P3

(12) United States Plant Patent
Roberts

(10) Patent No.: US PP25,108 P3
(45) Date of Patent: Nov. 25, 2014

(54) MINT PLANT 'MEADOW MINT'

(50) Latin Name: ***Mentha* sp.**
Varietal Denomination: Meadow Mint

(71) Applicant: Essex Laboratories, Inc., Napavine, WA (US)

(72) Inventor: Donald D. Roberts, Independence, OR (US)

(73) Assignee: Essex Laboratories, Inc., Napavine, WA (US)

( * ) Notice: Subject to any disclaimer, the term of this patent is extended or adjusted under 35 U.S.C. 154(b) by 0 days.

(21) Appl. No.: 13/986,037

(22) Filed: Mar. 25, 2013

(65) Prior Publication Data

US 2014/0289917 P1 Sep. 25, 2014

(51) Int. Cl.
*A01H 5/00* (2006.01)

(52) U.S. Cl.
USPC ..... Plt./259

(58) Field of Classification Search
USPC ..... Plt./259
See application file for complete search history.

(56) References Cited

U.S. PATENT DOCUMENTS

PP11,788 P2 * 2/2001 Roberts ..... Plt./259
PP13,720 P2 4/2003 Roberts

OTHER PUBLICATIONS

Gobert, V., "Hybridization in the section Mentha (Larniaceae) inferred from AFLP markers," Am. J. Bot. Dec. 2002, 89 (12), pp. 2017-2023.
Fuchs, Sabine, et al., "Biosynthesis of Menthofuran in Mentha × piperita; Stereoselective and Mechanistic Studies"; J. Agric. Food Chem., 1999, 47 (10), pp. 4100-4105.
Dung, Jeremiah K.S., et al, Evaluation of Verticillum Wilt Resistance in *Mentha arvensis* and *M. longifolia* Genotypes, Plant Disease, Oct. 2010, vol. 94, pp. 1255-1260.
Rohloff, Jens, et al., Effect of Harvest Time and Drying Method on Biomass Production, Essential Oil Yield, and Quality of Peppermint (*Mentha piperita* L.); J. Agric. Food Chem., 2005, 53 (10), pp. 4143-4148.
Rohloff, Jens, Monoterpene Composition of Essential Oil from Peppermint (*Mentha piperita* L.) with Regard to Leaf Position Using Solid-Phase Microextraction and Gas Chromatography/Mass Spectrometry Analysis; J. Agric. Food Chem.; 1999, 47(9), pp. 3782-3786.

* cited by examiner

*Primary Examiner* — June Hwu
*Assistant Examiner* — Keith Robinson
(74) *Attorney, Agent, or Firm* — Marger Johnson & McCollom, PC

(57) ABSTRACT

Mint selection 07-A3-11, denominated 'Meadow Mint', is a new *Mentha* sp. cultivar that produces an essential oil different in composition, produces more oil on a dry weight basis and has a branching pattern, large leaf size and resistance to mint rust (*Puccinia menthae*).

2 Drawing Sheets

Latin name of the genus and species: *Mentha* sp.
Variety denomination: 'MEADOW MINT'.

FEDERAL SPONSORSHIP

None

TYPE OF PLANT AND NAME OF VARIETY

The present invention relates to a new and distinct variety of peppermint plant developed from a parent of the species *Mentha arvensis*. The new variety will be identified as 'Meadow Mint'.

BACKGROUND OF THE INVENTION

This new mint was developed in a mint breeding program in which the primary objective was to develop a Mitcham type peppermint variety having a specific oil composition, acceptable yield and resistant to mint diseases. The new variety is as susceptible to mint wilt (soil borne fungus *Verticillium dahliae*) as its parent, but more resistant to mint rust (airborne fungus *Puccinia menthae*). Selection 07-A3-11 has a higher yield of oil than the control variety, 'Black Mitcham', in test plots since 2008. This plant was selected from a population of mint seedlings in research plots on land near Monmouth, Oreg. and initially identified as 07-A3-11.

DISCOVERY AND ASEXUAL REPRODUCTION

Selection 07-A3-11 originated as a seedling from an open pollinated *M. arvensis* (06-Blanco-11) female parent included with male fertile *M. piperita* (polyploid 'Black Mitcham') plants in a polycross breeding program. Selection 06-Blanco-11 is a first generation seedling from 'Blanco' (*M. arvensis*), a commercially grown variety for essential oil production. Diploid *M. piperita* is sterile and only becomes fertile in the polyploidy state. The parent plants in the polycross breeding system were composed of selected fertile male and female genotypes based on certain desirable characteristics.

Selection 07-A3-11 is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. Under the inventor's direction, Premier Botanicals has conducted asexual propagation of 07-A3-11 for greenhouse and field planting in Monmouth, Oreg., each year since 2007 and the genotype comes true to form with each generation.

SUMMARY OF THE INVENTION

Mint selection 07-A3-11, denominated 'Meadow Mint', is a new *Mentha* sp. cultivar that produces an essential oil different in composition than commercially grown mint varieties. The essential oil is similar to standard mint oil in components composition but differs in the typical ratio of components. Organoleptically it differs from typical *M. piperita* ('Black Mitcham') peppermint oil. It is more resistant to mint rust than current commercially grown M. arvensis varieties.

BRIEF DESCRIPTION OF THE PHOTOGRAPHS

The accompanying color photographs show typical, field grown vegetative growth of 07-A3-11 and depicts the color as nearly as reasonably possible.

Photograph 1 illustrates the growth habit under field conditions of my new mint plant.

Photograph 2 illustrates the leaf shape and color of my new mint plant.

DESCRIPTION OF PLANT

My new mint plant improves upon and is distinct from other mint plants in several characteristics, including but not limited to, the following:

1. The ability to produce an essential oil different in composition than typical commercial *M. arvensis*, ('Shivalik'), but with similar components as 'Black Mitcham' peppermint (*M. piperita*);
2. The ability to produce more oil on a dry weight basis than currently grown mint varieties;
3. A more vigorous plant but with a branching pattern similar to its parent;
4. A leaf larger than its parent, commercial *M. arvensis* ('Blanco'), and commercial *M. piperita* ('Black Mitcham');
5. A level of resistance to mint rust (*Puccinia menthae*) equal to or greater than that of its *M. arvensis* female parent;

The essential oil extracted from 07-A3-11 has a composition of components more like that of commercial oil produced by commercial *M. arvensis* ('Shivalik') than that of *M. piperita* ('Black Mitcham') as illustrated in Table 1. However, the ratio of oil components in 07-A3-11 is different from those of both *M. arvensis* and *M. piperita*. The concentration of menthone in oil of 07-A3-11 is greater than that of *M. arvensis* and *M. piperita*. There is only a trace of menthofuran present in the oil of 07-A3-11 and absent in oil of its parent *M. arvensis*. There is a trace of menthyl acetate in the essential oil of 07-A3-11 whereas, the component is present at 2.9% or greater in the parent seedling and commercial *M. arvensis* and *M. piperita*. Organoleptically, the oil of 07-A3-11 is different from that of Black Mitcham and *M. arvensis*, reflecting the difference in oil component ratios. Fragrance from the leaf is a pungent peppermint, lacking the strong menthol note of 'Shivalik' but more pronounced than 'Black Mitcham'.

TABLE 1

A Comparison of 07-A3-11 Essential Oil collected from test plots near Monmouth, Oregon, to that of its *M. arvensis* parent, Commercial *M. arvensis*, and Commercial *M. piperita* Oils. 1/

| Essential Oil Components | 06-Blanco-11 *Mentha arvensis* Parent seedling 2/ | 07-A3-11 Seedling 2/ | 'Shivalik' Commercial *M. arvensis* | 'Black Mitcham' Commercial *M. piperita* |
|---|---|---|---|---|
| 1-Limonene | 3.0 | 2.2 | 3.0 | 1.7 |
| 1,8-Cineole | <1.0 | <1.0 | <1.0 | 4.9 |
| 1-Menthone | 15.7 | 28.4 | 7.3 | 19.4 |
| Menthofuran | 0.0 | <1.0 | 0.0 | 4.2 |
| Isomenthone | 3.5 | 3.1 | 3.6 | 3.1 |
| 1-Menthyl Acetate | 3.7 | <1.0 | 2.9 | 5.3 |
| 1-Menthol | 64.3 | 59.1 | 73.9 | 44.6 |
| Pulegone | <1.0 | 0.0 | 0.0 | 2.1 |

The numbers listed in the above table are percentages based upon the analysis of the respective mint oils by gas chromatography. The percentages are determined by calculation of the relative peak areas.

1/ Commercial oils of *M. arvensis* ('Shivalik') and *M. piperita* ('Black Mitcham') were samples of what is typically produced by mint growers.

2/ The essential oil of *M. arvensis* parent seedling (06-Blanco-11) and 07-A3-11 were collected from plants growing in test plots in 2008.

TAXONOMIC DESCRIPTION OF 07-A3-11

This new plant, under greenhouse and field growing conditions, is an upright, bush type plant (Photograph 1) with lateral branches at each node of the main stem. It spreads from underground stolons. The height of 07-A3-11 is greater than 'Black Mitcham', growing under similar field conditions, reaching an average height of 1.3 m, and will vary based on fertilizer, soil quality, water application, amongst other known factors that affect growth patterns. Isolated as a single plant the height is 1.15 to 1.5 m with a width of 0.3 to 0.4 m. The main stem at mid-plant (approximately between the eleventh and twelfth node) of a mature plant is 4.5 mm-5.8 mm in width. The secondary and tertiary branch stems are 2.0 mm-3.2 mm and 1 mm-2 mm respectively.

Mature leaves at the bottom of the plant are ovate lanceolate. Leaves on upper mature plants, both main and secondary stems are more lanceolate (Photograph 2). Leaves on the mid-main and lower stem tend to be dentate like 'Black Mitcham' peppermint leaves, while leaves on the upper part of the plant, tend to be more dentate than 'Black Mitcham' peppermint. The serration of the main stem leaves have 14 to 16 teeth on each side of the leaf, while those on secondary branches and on flowering tip may be 7-10 teeth. Leaf dimensions at mid-plant (eleventh node) are 4.8 cm to 5.4 cm in width and 9.5 cm to 11 cm in length. Leaves on lateral branches and upper part of plant are 4 cm-4.5 cm in width and 7 cm-8 cm in length. The leaf is green in color ranging from The Fifth Edition Royal Horticultural Society Colour Chart 137A to 137B in the Fan 3 Green Group classification. The leaf has 6 to 8 lateral veins, more or less in parallel off the main vein that runs from the petiole to the tip of the leaf. The veins are prominent in all leaves of 07-A3-11. The leaf surface of both the bottom and top of the leaf is sub-glabrose, with the veins on the bottom surface being slightly more hairy. Oil glands are scattered across the surface of the underside of the leaf. Seed produced by 07-A3-11 varies in color from brown (Fifth Edition Royal Horticultural Society Colour Chart 177A, Fan 4 Greyed-Orange Group) to black (Fifth Edition Royal Horticultural Society Colour Chart 203B, Fan 4 Black Group), are oval in shape, ranging from 0.4 to 0.6 mm in width and from 0.6 to 0.8 mm in length.

The inflorescence is a conspicuous spike with capitates flowers developing at the nodes of the spike stem. The cylindrical spikes are about 30 mm in diameter and indeterminate in growth. The capitates flowers are 15-20 mm in width and 10-15 mm in length. The flowers consist of five petals fused into a two lipped corolla. The corolla is white in color as illustrated in The Fifth Edition Royal Horticultural Society Colour Chart NN155C in the Fan 4 White Group. The calyx is generally yellow green and is 142A to 142B, in the Fan 3 Green Group, as illustrated in The Fifth Edition Royal Horticultural Society Colour Chart index. The gynoecium consists of a single pistil with two lobed stigma that is exserted. The androecium consists of four stamens, each with a distinct filament and anther.

While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of mint plant, substantially as shown and described, characterized particularly by improved vigor, leaf size, and producing a unique essential oil.

* * * * *

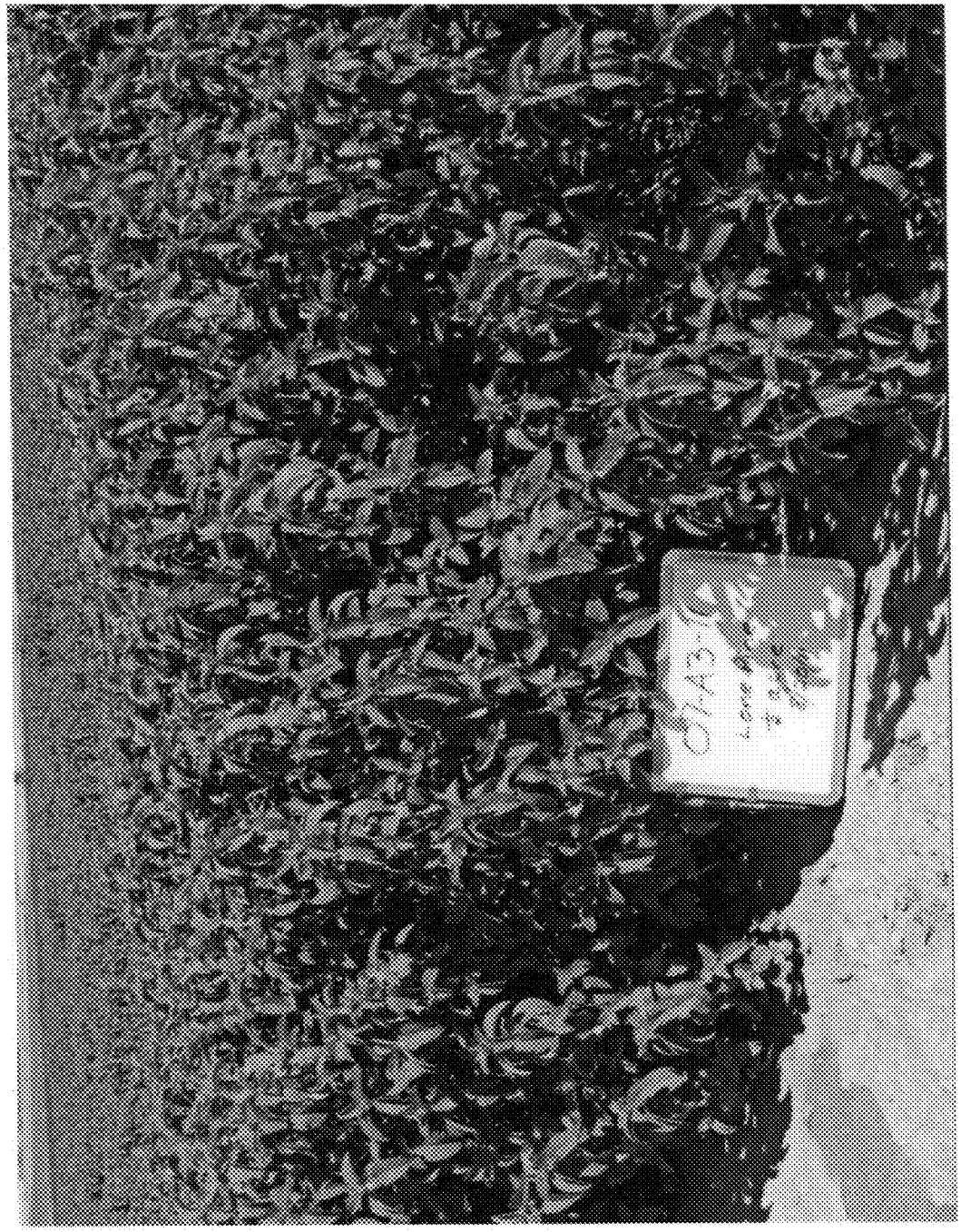

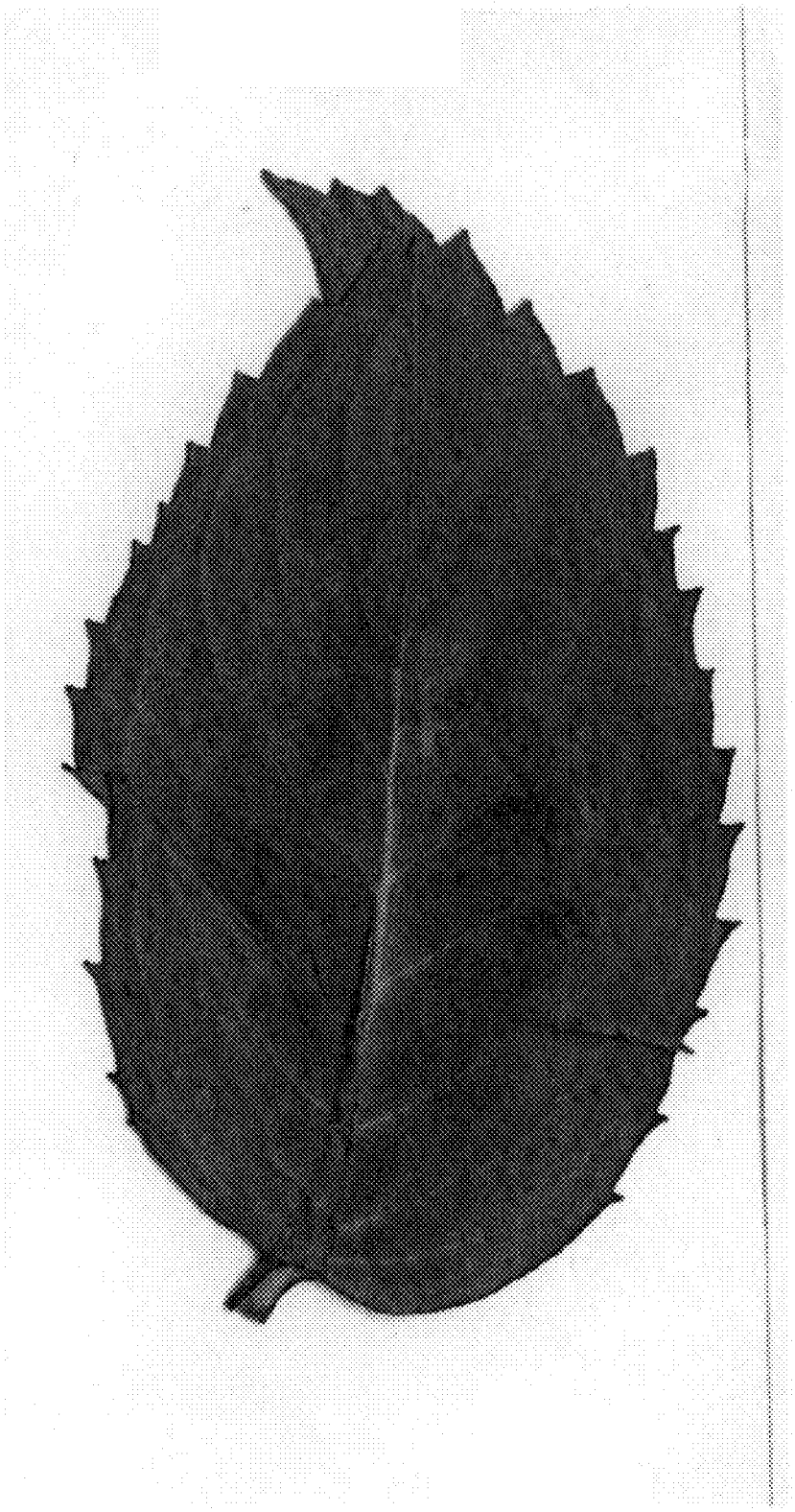
07-A3-11